US00PP29354P2

(12) United States Plant Patent
Egger

(10) Patent No.: US PP29,354 P2
(45) Date of Patent: Jun. 5, 2018

(54) ***HEUCHERA* PLANT NAMED 'TOPAZ JAZZ'**

(50) Latin Name: ***Heuchera* hybrid**
Varietal Denomination: Topaz Jazz

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days. days.

(21) Appl. No.: 15/530,993

(22) Filed: Apr. 4, 2017

(51) Int. Cl.
*A01H 5/12* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Klarquist Sparkman, LLP

(57) ABSTRACT

A new and distinct *Heuchera* plant characterized by leaves which are multicolored changing from peach to gold with a strong veil overall, medium size, lobed leaves, yellow green flowers on short flowering stems, a medium mounding habit, and excellent vigor.

1 Drawing Sheet

Botanical denomination: *Heuchera* hybrid.
Variety designation: 'Topaz Jazz'.

BACKGROUND OF THE INVENTION

The present invention relates to a new and distinct cultivar of *Heuchera* and given the cultivar name of 'Topaz Jazz'. *Heuchera* is in the family Saxifragaceae. *Heuchera* 'Topaz Jazz' originated as a controlled cross using *Heuchera* 'K873-2', a proprietary, unpatented, unnamed plant as the seed parent, and *Heuchera* 'K853-1', a proprietary, unpatented, unnamed plant as the pollen parent.

Compared to the seed parent, *Heuchera* 'K873-2', the new cultivar has a larger habit and the flowering stem attitude is upright rather than side-facing.

Compared to the pollen parent, *Heuchera* 'K853-1', the new cultivar has yellow green flowers rather than green and the leaves are veiled rather than not veiled.

Compared to *Heuchera* 'TNHEUCHA', U.S. Plant Pat. No. 27,567, the new cultivar has smaller leaves that are more lobed and undulate and a tighter habit with more crowns. The flowers of the new cultivar are yellow green rather than light salmon pink and are more upright growing.

Compared to *Heuchera* 'Ginger Ale', U.S. Plant Pat. No. 18,173, the new cultivar has a larger leaves, with a stronger white veil, and are more undulate in brighter colors. The inflorescences are shorter in the new cultivar and are not leafy as are the peduncles of 'Ginger Ale'.

This new *Heuchera* is uniquely distinguished by:

1. leaves which are multicolored changing from peach to yellow green with a strong white veil overall,
2. medium large, palmately lobed leaves,
3. yellow green flowers on upright short flowering stems,
4. a medium mounding habit, and
5. excellent vigor.

This new cultivar has been reproduced only by asexual propagation (tip cuttings and tissue culture using growing tips). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
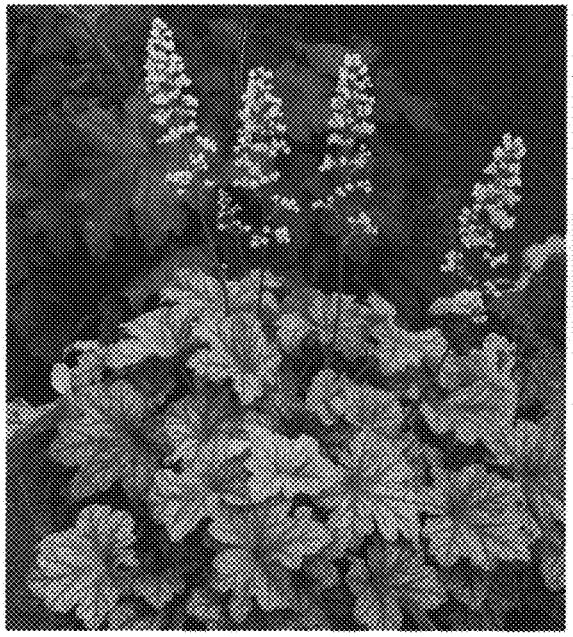
FIG. 1 shows a nine-month-old plant of *Heuchera* 'Topaz Jazz' growing in the trial bed in September in Canby, Oreg.
Figure 2:
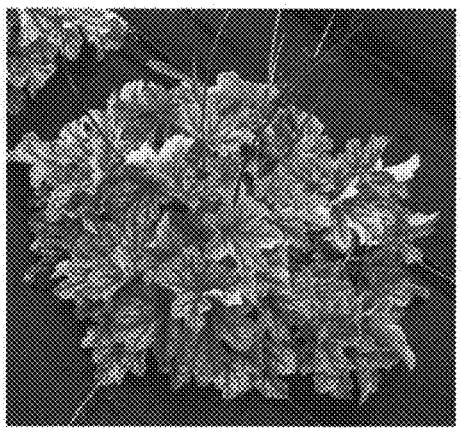
FIG. 2 shows the same plant in February.
Figure 3:
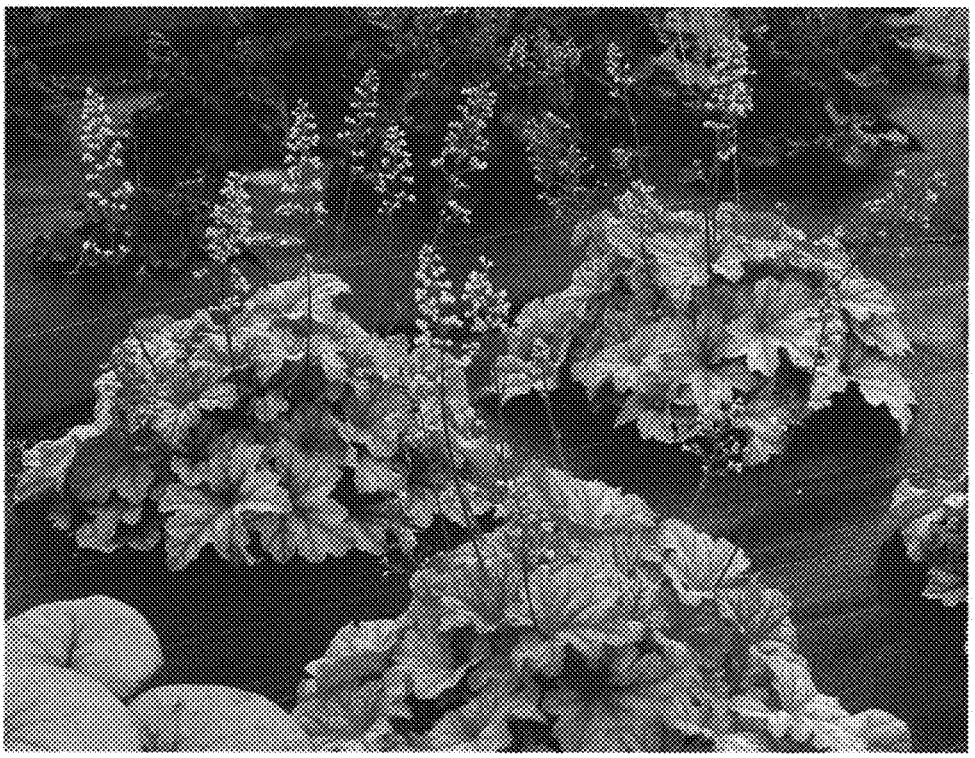
FIG. 3 shows the new cultivar in mid-summer in the trial beds in Canby, Oreg.

The following is a detailed description of the new *Heuchera* cultivar based on observations taken in April of one-year-old specimens growing in one gallon containers in a covered, unheated greenhouse in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* $5^{th}$ edition, 2007.

Plant:

*Form.*—Basal rosette, herbaceous perennial.
*Hardiness.*—USDA Zone 4 to 9.
*Size.*—21 cm tall from top of the foliage to the ground and 38 cm wide.
*Number of crowns.*—10.
*Habit.*—Mounding.
*Vigor.*—Excellent.

Leaf:

*Type.*—Simple.
*Arrangement.*—Rosette.
*Shape.*—Broadly ovate to orbicular.

*Number*.—About 110.
*Blade size*.—Grows to 11 cm long and 12 cm wide.
*Venation*.—Palmate.
*Lobing/division*.—7 palmate lobes, with shallow secondary lobes.
*Margins*.—Crenate, mildly undulate.
*Apex*.—Mucronulate.
*Base*.—Cordate, strongly overlapping and sometimes spiraling in.
*Surface texture*.—Glandular-puberulent on both sides.
*Leaf rugosity*.—Absent.
*Petiole description*.—Grows to 14 cm long and 3.5 mm wide, glandular hairs, Greyed Red 182B.
*Leaf color*.—Grows to 16 cm long and 2.5 mm wide, glandular hairs, Greyed Red 182B.
*Leaf color*.—Variable, depending on light and temperature; spring topside, new leaves Greyed Orange 178B with a strong veil that covers all but veins and margins, closest to Greyed Orange 177C, bottom side Greyed Purple 185B, mature leaves Greyed Orange 165B and 165C with veins 165A, bottom side Greyed Orange 165C near margins then tinted 185B toward the center; summer and fall topside, Greyed Orange 167A to 161A on margins and veins with vein closest to 161D to Yellow Green 150D, bottom side Greyed Red 182C; winter topside closest to Greyed Red 182C with vein Greyed Purple 183B (lightning to Yellow Orange 19B with vein Greyed Red 179A), bottom side closest to Greyed Red 182C.

Inflorescence:
*Size*.—Grows to 4.5 cm wide and 11 cm long.
*Type*.—Upright thyrse.
*Number of flowers per thyrse*.—About 150.
*Number of thyrse*.—About 20.
*Peduncle*.—Grows to 28 cm long and 4 mm wide at base, glandular hairs, Greyed Red 178A.
*Pedicel*.—Grows to 4 mm long, with glandular hairs, Yellow Green 152C.
*Bloom period*.—Spring to fall.

Flower bud:
*Size*.—3 mm wide and 5 mm long.
*Description*.—Glandular puberulent, ovoid, down facing.
*Color*.—Yellow Green 151A.

Flower:
*Type*.—Perfect.
*Shape*.—Campanulate.
*Attitude*.—Side-facing.
*Size*.—5 mm long and 6 mm wide.
*Corolla description*.—5 petals, each 3 mm long and 1.3 mm wide, spatulate, 1-to 2-notched near tip, margins entire, tip acute, glandular-puberulent and White NN155A on both sides.
*Calyx description*.—Campanulate, 5 mm long and 6 mm wide, with 5 lobes with wide sinuses divided ½ way to the base, each 2 mm wide and 3 mm long, oblong in shape, back side glandular-puberulent, glabrous inside, tip obtuse, margin entire, Yellow Green 151A on both sides.
*Stamen description*.—5 in number, filaments 3 mm long, White NN155A, anthers 0.4 mm long, Orange 26A, no pollen.
*Pistil description*.—1, 2-beaked, 4 mm long and 2 mm wide, Yellow Green N144A overall, ovary 2 mm long and 2 mm wide, style 2 mm long.
*Fragrance*.—None.
*Lastingness*.—Each thyrse blooms for about 3 weeks on the plant.

Fruit and Seed: None seed, infertile.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *